US010099009B1

(12) United States Patent
Anderson

(10) Patent No.: US 10,099,009 B1
(45) Date of Patent: Oct. 16, 2018

(54) CENTRAL VENOUS CATHETER WITH REVERSE FLUSH PORT

(71) Applicant: Judith L. Anderson, Shawnee, KS (US)

(72) Inventor: Judith L. Anderson, Shawnee, KS (US)

( * ) Notice: Subject to any disclaimer, the term of this patent is extended or adjusted under 35 U.S.C. 154(b) by 190 days.

(21) Appl. No.: 15/064,224

(22) Filed: Mar. 8, 2016

Related U.S. Application Data

(60) Provisional application No. 62/132,108, filed on Mar. 12, 2015.

(51) Int. Cl.
*A61M 5/168* (2006.01)
*A61M 39/22* (2006.01)

(52) U.S. Cl.
CPC .... *A61M 5/16804* (2013.01); *A61M 5/16813* (2013.01); *A61M 39/225* (2013.01)

(58) Field of Classification Search
CPC .......... A61M 5/16804; A61M 5/16827; A61M 5/16813; A61M 39/225; A61M 39/223
See application file for complete search history.

(56) References Cited

U.S. PATENT DOCUMENTS

| 4,219,021 A | 8/1980 | Fink |
| 4,257,416 A | 3/1981 | Prager |
| 4,954,129 A | 9/1990 | Giuliani et al. |
| 5,053,003 A | 10/1991 | Dadson et al. |
| 5,439,452 A | 8/1995 | McCarty |
| 5,772,625 A | 6/1998 | Krueger et al. |
| 5,795,340 A | 8/1998 | Lang |
| 6,508,778 B1 | 1/2003 | Verkaart et al. |
| 7,662,110 B2 * | 2/2010 | Flaherty .............. A61M 5/1407 600/486 |
| 7,892,210 B2 | 2/2011 | Ranalletta et al. |
| 2008/0058768 A1 | 3/2008 | Gonzales |
| 2009/0281486 A1 * | 11/2009 | Ducharme ............. A61B 1/018 604/58 |

* cited by examiner

*Primary Examiner* — Laura Bouchelle
*Assistant Examiner* — Tasnim M Ahmed
(74) *Attorney, Agent, or Firm* — Erickson Kernell IP, LLC

(57) ABSTRACT

A catheter having a secondary port that enables flushing a fluid from a portion of the catheter. The secondary port is disposed along the length of the catheter tube so as to be near an entry point of the catheter into a patient's body. A clamp is disposed adjacent to the secondary port on a side proximate to the patient's body. The secondary port and clamp enable flushing of a fluid from a portion of the catheter that is external to the patient's body and disposal of a clot- or obstruction-dissolving agent into the external portion of the catheter. Upon removal of the clot or obstruction, the secondary port and clamp enable removal of the dissolving agent and replenishing the fluid in the external portion of the catheter to resume provision of the fluid to the patient.

9 Claims, 4 Drawing Sheets

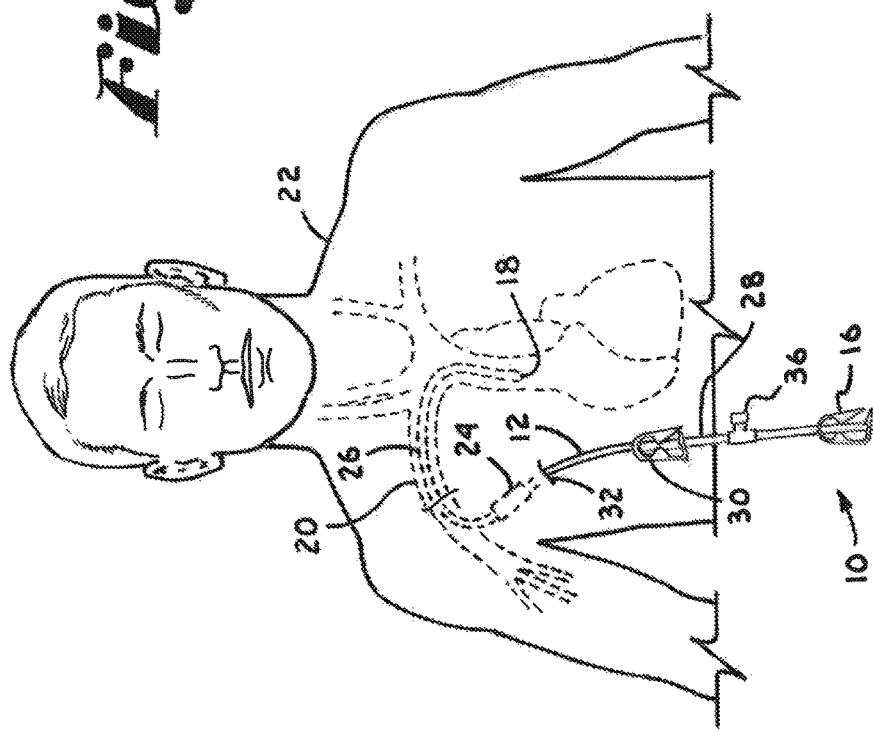
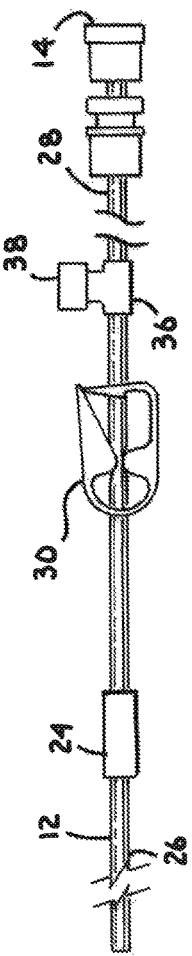

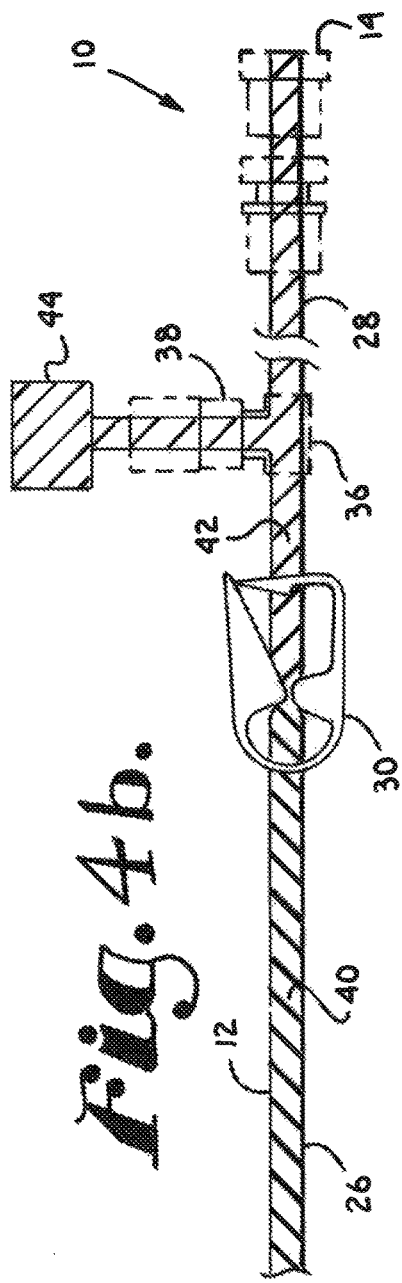
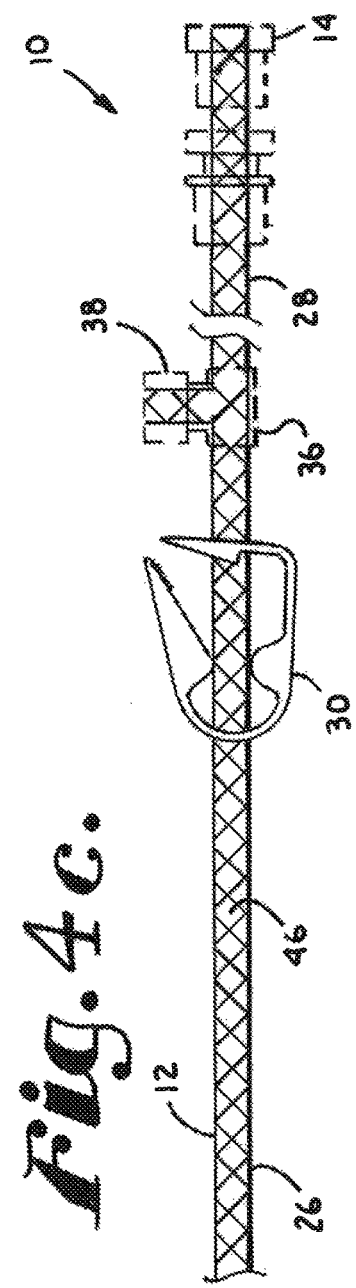

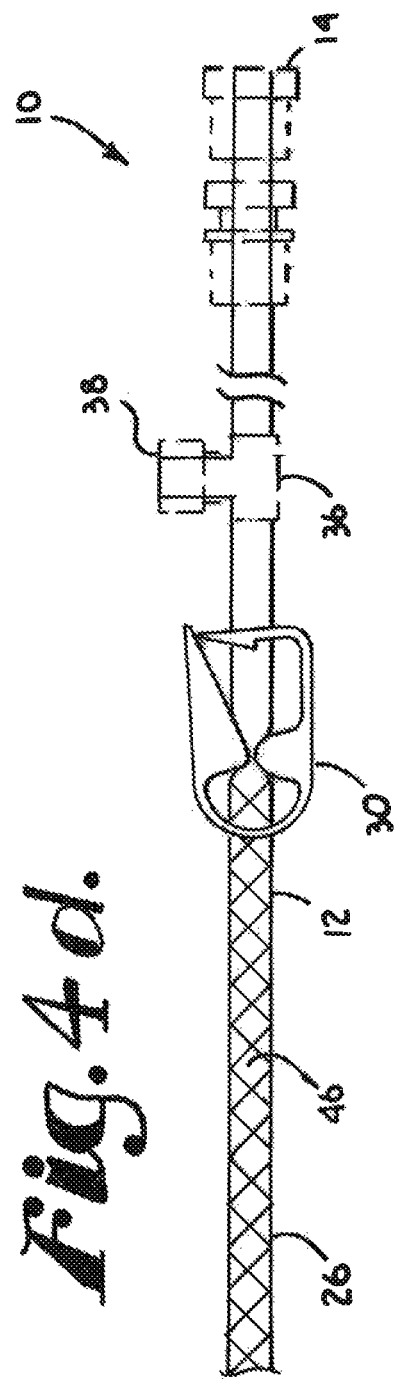

CENTRAL VENOUS CATHETER WITH REVERSE FLUSH PORT

CROSS-REFERENCE TO RELATED APPLICATIONS

This application claims the benefit of U.S. Provisional Patent Application No. 62/132,108 filed Mar. 12, 2015, the disclosure of which is hereby incorporated herein in its entirety by reference.

BACKGROUND

Central venous catheters or central line catheters are commonly used to administer medications, fluids, nutrients, blood products, and the like to patients. The central line catheter comprises a section of tubing that is inserted into a vein, such as the jugular vein in the neck, the subclavian vein in the chest, or a large vein in the arm and is threaded through the vein until it reaches a desired location in the body, such as the heart or a major organ. The catheter can be left in place for a longer period of time, e.g. weeks or months, than standard intravenous catheters or IVs inserted near the surface of the skin.

A problem that is often encountered with central line catheters is the formation of clots or occlusions within the lumen or around the end of the tube. The clots can result from precipitation of solids from fluids in the catheter, thrombosis in or around the catheter, and fibrin formation on the catheter walls, among others.

Clots and occlusions are treated by periodically flushing the catheter with chemicals configured to dissolve the clot or occlusion. For example, tPA (Tissue plasminogen activator) or rtPA (recombinant tissue plasminogen activator), alteplase, and recombinant urokinase are often employed to dissolve thrombolytic clots and fibrins while solutions of varied pH are employed to dissolve clots formed from precipitates. These de-clotting agents are typically forced into the catheter, such as by applying fluid pressure via a syringe loaded with the de-clotting agent, to fill any available space within the catheter with the de-clotting agent. In some practices, a vacuum is drawn on the clotted catheter using an empty syringe to collapse the catheter tubing and thereby provide additional space within the catheter in which the de-clotting agent can be disposed. Once in the catheter, the de-clotting agent is allowed to mix with and diffuse into any fluids in the catheter and to dissolve the clots or occlusions over a period of time. The de-clotting agents can then be withdrawn from the catheter and replaced with desired medicinal fluids or allowed to infuse into the body along with the medicinal fluids provided via the catheter.

Current practices of forcing the de-clotting agents into the catheter can also cause medicinal fluids that are in the catheter to be forced into the body. This can result in an unwanted bolus of medicine being provided to a patient and potentially an overdose condition in the patient. Depending on the medication, the patient may become very ill or suffer other deleterious effects from such a bolus.

SUMMARY

Embodiments of the invention are defined by the claims below, not this summary. A high-level overview of various aspects of the invention are provided here for that reason, to provide an overview of the disclosure, and to introduce a selection of concepts that are further described in the Detailed-Description section below. This summary is not intended to identify key features or essential features of the claimed subject matter, nor is it intended to be used as an aid in isolation to determine the scope of the claimed subject matter. In brief, this disclosure describes, among other things, an apparatus and methods for de-clotting an intravenous catheter that reduces or eliminates unwanted provision of medicinal fluids to a patient.

In an embodiment, the apparatus comprises a catheter, such as a central line catheter, having a clamp or valve along the length of the catheter tube external to a patient's body and near a fixation cuff on the catheter. A secondary port is provided adjacent to the clamp/valve and is located on a distal side of the clamp/valve, e.g. on a side of the clamp/valve that is nearest to a fluid dispensing apparatus and opposite the clamp/valve from the patient.

When closed, the clamp restricts the flow of fluids into the body and defines an intravenous or proximal portion of the tube that is inserted in the body and an external or distal portion that is external to the body. The secondary port allows backflushing of the external portion to remove medication contained therein. The external portion can thus be filled with a de-clotting agent either through the port or through a first end of the catheter. The clamp is subsequently opened to allow infiltration of the de-clotting agent into the liquid contained in the intravenous portion of the tube to dissolve any clots from the intravenous portion. After the clot is dissolved, the solution is withdrawn from the first end of the catheter and the cleared tube can then be used to deliver medicine as intended. Using this system, the de-clotting agent is introduced to the intravenous portion of the tube without forcing additional fluid from the catheter into the body.

DESCRIPTION OF THE DRAWINGS

Illustrative embodiments of the invention are described in detail below with reference to the attached drawing figures, and wherein:

FIG. 1 is a schematic view of the intravenous catheter with a flushing port installed in a subclavian vein of a patient in accordance with an embodiment of the invention;

FIG. 2 is a side elevational view of the intravenous catheter of FIG. 1 depicted in accordance with an embodiment of the invention;

FIG. 4B is a diagrammatic side view of the intravenous catheter of FIG. 1 depicting a clamp in a closed position and a flow of flushing solution into a secondary port on the catheter and into an external portion of the catheter;

FIG. 4C is a diagrammatic side view of the intravenous catheter of FIG. 1 depicting a clamp in an open position and a flushing solution diffused into a fluid within an internal portion of the catheter; and FIG. 4D is a diagrammatic side view of the intravenous catheter of FIG. 1 depicting a clamp in a closed position with a mixture of flushing solution and fluid in an internal portion of the catheter and an empty external portion of the catheter.

DETAILED DESCRIPTION

Figure 3:
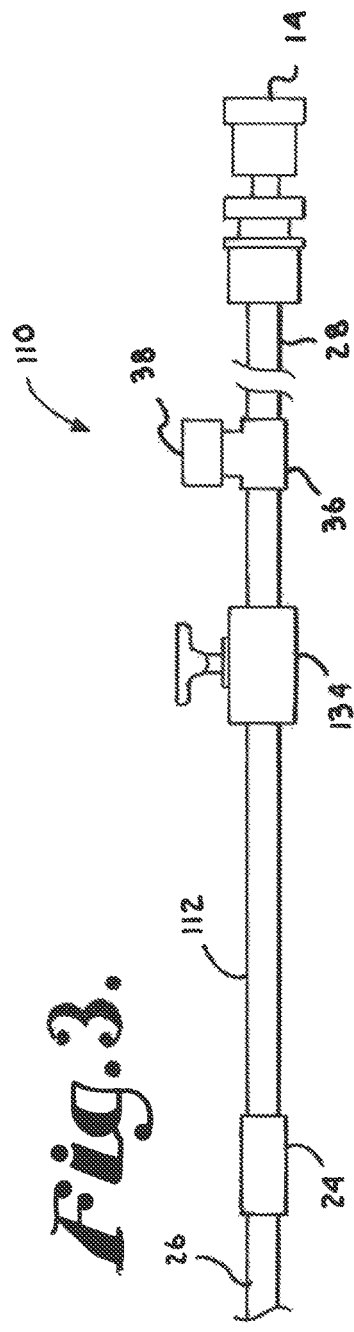
FIG. 3 is a side elevational view of an intravenous catheter with a flushing port that includes a valve depicted in accordance with another embodiment of the invention.

The subject matter of select embodiments of the invention is described with specificity herein to meet statutory requirements. But the description itself is not intended to necessarily limit the scope of claims. Rather, the claimed subject matter might be embodied in other ways to include different components, steps, or combinations thereof similar to the ones described in this document, in conjunction with other present or future technologies. Terms should not be interpreted as implying any particular order among or between various steps herein disclosed unless and except when the order of individual steps is explicitly described.

Various embodiments of the invention are described herein with respect to the drawings in which reference numerals are employed to identify particular components or features. Similar elements in the various embodiments depicted are provided with reference numerals having matching second and third digits but with differing first digits, e.g. element 10 is similar to elements 110, 210, etc. Such is provided for clarity and to avoid redundancy but is not intended to indicate that the particular features or elements are necessarily the same. It is also to be understood that the drawings and/or objects depicted therein are not necessarily drawn to scale.

Embodiments of the invention are described herein with respect to a central venous catheter or central line catheter however, it is understood that the technology can be applied to other types of catheters without departing from the scope described herein. Embodiments of the invention are described with respect to use with humans and human bodies, but it is recognized that embodiments of the invention can also be employed in non-humans. The catheters can be employed in a variety of types of catheter installations including peripherally inserted central catheters (PICC) and tunneled catheters among a variety of others.

With reference now to the drawings, and to FIGS. 1-2 in particular, an intravenous catheter 10 is described in accordance with an embodiment of the invention. The catheter 10 comprises an elongate tube 12 having a primary port 14 disposed at a distal end thereof. The primary port 14 is a port that is available in the art and is configured to couple to one or more of a syringe, a medication pumping or dispensing apparatus, a reservoir for receiving liquids for disposal, or the like. A clamp 16, valve, or other flow-restricting device can be provided near the primary port 14 or integral with the primary port 14 to restrict flow of fluids from the primary port 14 when disconnected from a syringe or other dispensing apparatus.

A proximate end 18 of the catheter is configured for insertion into a vein 20 in a patient's body 22, such as a jugular vein, subclavian vein, or large vein in an arm of the patient, among others. A cuff 24, tabs, adhesive material, or other securement feature may be provided along the length of the catheter tube 12 and generally divides the catheter tube 12 into a proximate or internal portion 26 that is inserted inside the patient's body and a distal or external portion 28 that remains outside the patient's body. The cuff 24 may be installed under the skin of the patient and attached or adhered thereto, such as by using one or more sutures, or may remain external to the body 22 and affixed thereto via one or more adhesive tabs, bandages, or the like.

A second clamp 30 is disposed distal to and in close proximity to the cuff 24 and/or to an entry point 32 of the catheter 10 into the patient's body 22, e.g. between the cuff 24 and the primary port 14. The second clamp 30 comprises a clamp available in the art that is configured to restrict flow of liquids or gases through the tube 12 when the clamp 30 is in a closed position and to enable flow through the tube 12 when in an open position. In another embodiment depicted in FIG. 3, a valve 134, petcock, or other device that is selectively actuatable to restrict flow of fluids through the tube 112 is used in place of the second clamp 30.

A secondary port 36 is provided distal to and in close proximity to the second clamp 30, e.g. between the clamp 30 and the primary port 14 along the external portion 28. The secondary port 36 is in fluid communication with the interior of the tube 12 to enable fluids in the tube 12 to flow out of the secondary port 36 or vice-versa. The secondary port 36 includes a coupling 38 that is configured to couple to a syringe or other fluid-dispensing or fluid-receiving apparatus as known in the art and may include a shut-off valve to selectively restrict flow of fluids through the secondary port 36 when the port 36 is not coupled to such an apparatus. The junction between the secondary port 36 and the tube 12 can be configured as a T-, Y-, or other style junction.

The external portion 28 of the tube 12, e.g. the portion between the secondary port 36 and the primary port 14 can vary in length from several inches to several feet depending on a desired configuration and/or application. Such lengths may be desirable to provide sufficient reach of the tubing 12 to couple to a fluid dispensing apparatus. Additionally, it is often desirable to provide a small excess of the tubing 12 that can be affixed to the patient's body 22 to relocate any disturbances of the tubing 12 from the entry point 32 to the excess tubing. Thereby stresses and/or irritations of the skin around the entry point 32 may be reduced. And risks of the internal portion 26 of the tube 12 being moved during handling of the external portion 28 can be at least partially abated.

Figure 4A:
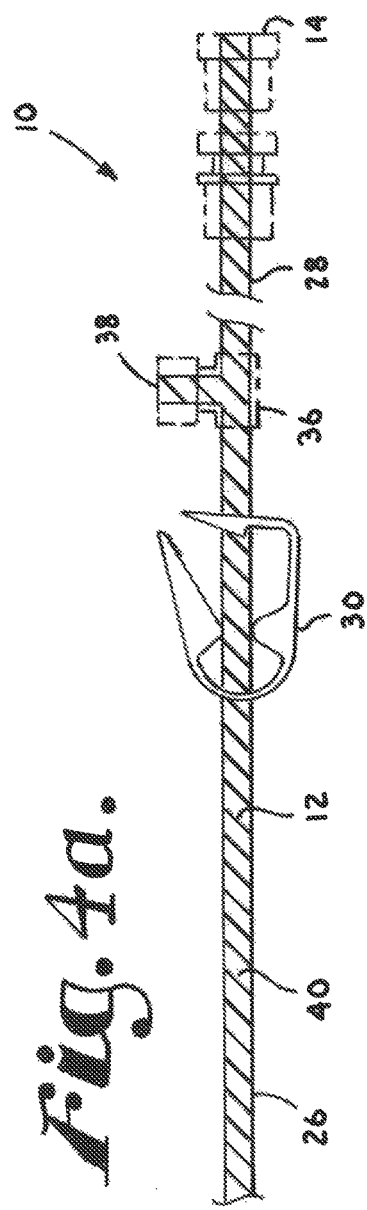
FIG. 4A is a diagrammatic side view of the intravenous catheter of FIG. 1 depicting a flow of fluid to a patient through the catheter.

With additional reference now to FIGS. 4A-D operation of the catheter 10 is described in accordance with an embodiment of the invention. Although not shown in FIGS. 4A-D for clarity, the catheter 10 is installed in a patient's body 22 such that the internal portion 26 is internal to the patient. FIG. 4A depicts use of the catheter 10 to provide fluids 40, such as hydration, nutrition, or medicinal fluids (hereinafter collectively referred to as "fluids 40") to a patient. As shown in FIG. 4A, the second clamp 30 is in an open position to enable the fluid 40 to flow from a dispensing apparatus (not shown) coupled to the primary port 14, through the tube 12, and from the proximate end 18 of the tube 12 into the patient's body 22. A first hatching pattern is depicted within the tube 12 to indicate the presence of the fluid 40.

The state of the catheter 10 depicted in FIG. 4A is a standard configuration for provision of the fluid 40 to the patient. During a course of treatment of the patient over a period of time, clots or other obstructions may form in the internal portion 26 of the tube 12 or on or around the proximate end 18 of the tube 12 that obstruct flow of the fluids 40 through the tube 12. These clots and obstructions should be dissolved using an appropriate flushing solution 42 in order to reopen the tubing 12 and to avoid a need to replace the catheter 10 which may require a surgical procedure and which exposes the patient to additional opportunities for infection, among other unwanted consequences.

The flushing solution 42 can be a solution available in the art like, for example, tPA (Tissue plasminogen activator) or rtPA (recombinant tissue plasminogen activator), alteplase, and recombinant urokinase which are often employed to dissolve thrombolytic clots and fibrins. The flushing solution 42 might also comprise a solution having an acidic or basic pH that is configured to dissolve precipitates forming obstructions in the tubing 12, among other solutions available in the art.

To remove the clots or obstructions (hereinafter collectively referred to as "clots") the fluid 40 is first removed from the external portion 28 of the tube 12. Removal of the fluid 40 may be advantageous because the fluid 40 obstructs direct application of the flushing solution 42 to the clot. Removal of the fluid 40 from the external portion 28 enables disposal of the flushing solution 42 into closer proximity to the clot thereby reducing time needed for the flushing solution 42 to infiltrate into the internal portion 26 of the tube 26 to reach the clot. Removal of the fluid 40 also prevents the fluid 40 from being unnecessarily forced into the patient's body 22.

Prior art practices often employ the application of fluid pressure on the catheter 10 to force a volume of the flushing solution 42 into the tube 12 and thereby force a volume of the fluid 40 into the patient to make way for the flushing solution 42. When the fluid 40 comprises, for example, a medicinal fluid, administration of such a volume of the fluid 40 to the patient can be very detrimental. Such a volume of the fluid 40 may create an overdose condition in the patient or have other negative side effects.

With continued reference to FIG. 4B, the second clamp 30 is placed in a closed position to restrict flow of the fluid 40 into and out of the internal portion 26 of the tube 12. A flushing solution dispenser 44, such as a syringe or other dispensing apparatus, is coupled to the secondary port 36. The flushing solution 42 is flowed through the secondary port 36 into the external portion 28 of the tube 12 to remove the fluid 40 from the external portion 28 and to fill the external portion 28 with the flushing solution 42. Alternatively, the flushing solution 42 might be disposed in the tube 12 via the primary port 14 and fluid 40 removed via the secondary port 36. In one embodiment, the primary or secondary port 36 is opened to enable air or a gas to enter the external portion 28 and thus allow the fluid 40 to be drained therefrom. A second hatching pattern is provided in FIG. 4B to indicate the presence of the flushing solution 44 in the external portion 28 of the tube 12.

Referring now to FIG. 4C, the second clamp 30 is placed in the open position to enable the flushing solution 42 in the external portion 28 to infiltrate or diffuse into the fluid 40 in the internal portion 26 of the tube 12 and thereby reach the clot to act thereon. A third hatching pattern is provided in FIG. 4C to indicate that the tube 12 is filled with a mixture 46 of the fluid 40 and the flushing solution 42. The catheter 10 may be allowed to remain in this configuration for a period of time while the clot is acted on by the flushing solution 42. There may be substantially no flow through the tube 12 during this period of time, or fluid pressure may be applied to force a volume of the mixture 46 through the tube 12 toward the proximate end 18 and thereby speed application of the flushing solution 42 to the clot. The catheter 10 may be periodically checked by applying positive or negative fluid pressure to determine whether the clot has been dissolved and fluid communication restored.

Upon removal of the clot, the second clamp 30 can again be closed and the mixture 46 removed from the external portion 28 of the tube 12. In one embodiment, negative fluid pressure may be applied to the catheter 10 prior to closing the second clamp 30 to withdraw the mixture from the internal portion 26 of the tube 12. The second clamp 30 can thus be closed upon full or partial removal of the mixture 46 from the internal portion 26. Such removal might be indicated by aspiration of blood into the tube 12 up to the second clamp 30 or into the external portion 28 of the tube 12.

The mixture 46 can be removed by opening the secondary port 36 to enable entry of air or a gas and flowing of the mixture 46 from the primary port 14, or vice-versa. As depicted in FIG. 4D, the mixture 46 remains in the internal portion 26 while the external portion 28 is empty. The mixture 46 might alternatively be flushed from the tube 12 in a manner similar to that described above with respect to FIG. 4B by flowing the fluid 40 or another fluid, e.g. a saline solution, into the primary port 14 to flush the mixture 46 out the secondary port 36, or vice-versa. In another embodiment, the mixture 46 might be retained in the tube 12 and administered to the patient in due course. The rate of such administration might be adjusted to accommodate any dilution of the fluid 40 by the flushing solution 42 in the mixture.

When necessary the primary port 14 is recoupled to the fluid dispensing apparatus. The fluid 40 is again flowed into the external portion 28 from the fluid dispensing apparatus to fill the external portion 28. The secondary port 36 is closed and/or disconnected from any receptacles employed to receive the fluid 40, the flushing solution 44, or the mixture 46 as the fluid 40 is reintroduced into the external portion 28. The second clamp 30 is opened to return the catheter 10 to the state depicted in FIG. 4A for normal operation and dispensation of the fluid 40 to the patient.

Many different arrangements of the various components depicted, as well as components not shown, are possible without departing from the scope of the claims below. Embodiments of the technology have been described with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

What is claimed is:

1. A method for removing a clot or obstruction from a central venous catheter, the method comprising:

administering a fluid to a living body via a catheter having a proximal portion and a distal portion defined by a port disposed therebetween along a length of a catheter tubing, the proximal portion being configured for insertion into the living body and the distal portion having a free end configured to couple to a fluid-delivery apparatus;

actuating a flow-restricting means to a closed position to restrict a flow of the fluid from the distal to the proximal portion of the catheter, the flow-restricting means being disposed on the proximal portion in close proximity to the port;

flowing a flushing solution into the distal portion via the port to replace the fluid in the distal portion with the flushing solution, the flushing solution being configured to dissolve the clot or obstruction formed in the proximal portion of the catheter;

actuating the flow-restricting means to an open position to enable fluid communication of the flushing solution from the distal portion to the proximal portion of the catheter;

diffusing the flushing solution in the distal portion into the fluid in the proximal portion over a period of time thereby forming a mixture of the flushing solution and the fluid within the distal and proximal portions of the catheter, the diffusing placing the flushing solution in communication with the clot or obstruction to enable the flushing solution to dissolve the clot or obstruction;

determining the presence of the clot or obstruction by applying one or both of a positive and a negative pressure on the mixture; actuating the flow-restricting means to the closed position when the clot or obstruction is determined to no longer be present;

removing the mixture of the flushing solution and the fluid from the distal portion of the catheter using the port and the free end of the distal portion;

refilling the distal portion with the fluid using the free end of the distal portion and the port; and actuating the flow-restricting means to the open position to resume administration of the fluid to the living body.

2. The method of claim 1, further comprising:

applying a negative fluid pressure on the catheter to draw the mixture of the fluid and the flushing solution from the proximal portion into the distal portion.

3. The method of claim 2, wherein applying a negative fluid pressure on the catheter to draw the mixture of the fluid and the flushing solution from the proximal portion into the distal portion comprises aspirating a bodily fluid from the living body at least partially into the catheter.

4. The method of claim 1, wherein the fluid comprises one or more of a medicinal fluid, a hydration fluid, and a nutrition fluid.

5. The method of claim 1, wherein fluid communication of the flushing solution from the distal portion to the proximal portion of the catheter includes applying a fluid pressure on the catheter to at least partially flow the flushing solution into the proximal portion.

6. The method of claim 1, wherein substantially none of the fluid is administered to the living body between actuating the flow-restricting means to the closed position to restrict the flow of the fluid from the distal to the proximal portion of the catheter and actuating the flow-restricting means to the open position to resume administration of the fluid to the living body.

7. The method of claim 1, wherein removing the mixture of the flushing solution and the fluid from the distal portion of the catheter using the port and the free end of the distal portion and refilling the distal portion with the fluid using the free end of the distal portion and the port further comprises:

opening the port or the free end to enable a gas to enter the distal portion;

draining the mixture from the distal portion via another of the port and the free end.

8. The method of claim 1, wherein removing the mixture of the flushing solution and the fluid from the distal portion of the catheter using the port and the free end of the distal portion and refilling the distal portion with the fluid using the free end of the distal portion and the port further comprises:

flowing the fluid into the distal portion using one of the port and the free end;

draining the mixture from the distal portion via another of the port and the free end.

9. The method of claim 1, wherein the flushing solution is one or more of tPA (Tissue plasminogen activator), rtPA (recombinant tissue plasminogen activator), alteplase, and recombinant urokinase.

* * * * *